united States Patent

US 10,384,009 B2

Olson et al.

(45) Date of Patent: Aug. 20, 2019

(54) SIGNAL DELAYING ASSEMBLY FOR A MEDICAMENT DELIVERY DEVICE

(71) Applicant: Carebay Europe Ltd., Swatar (MT)

(72) Inventors: Stephan Olson, Danderyd (SE); Daniel Sall, Segeltorp (SE)

(73) Assignee: SHL Medical AG, Zug (CH)

( * ) Notice: Subject to any disclaimer, the term of this patent is extended or adjusted under 35 U.S.C. 154(b) by 6 days.

(21) Appl. No.: 15/507,673

(22) PCT Filed: Aug. 18, 2015

(86) PCT No.: PCT/EP2015/068951
§ 371 (c)(1),
(2) Date: Feb. 28, 2017

(87) PCT Pub. No.: WO2016/034407
PCT Pub. Date: Mar. 10, 2016

(65) Prior Publication Data
US 2017/0368259 A1    Dec. 28, 2017

(30) Foreign Application Priority Data

Sep. 1, 2014 (SE) ...................................... 1451017

(51) Int. Cl.
*A61M 5/20* (2006.01)
*A61M 5/315* (2006.01)
(Continued)

(52) U.S. Cl.
CPC ........ *A61M 5/2033* (2013.01); *A61M 5/3157* (2013.01); *A61M 5/326* (2013.01);
(Continued)

(58) Field of Classification Search
CPC .............. A61M 5/3157; A61M 5/2033; A61M 5/3271; A61M 5/326; A61M 5/5086;
(Continued)

(56) References Cited

U.S. PATENT DOCUMENTS 4,561,856 A * 12/1985 Cochran ............... A61M 5/155
604/143
7,119,593 B2    10/2006 Gower et al.
(Continued)

FOREIGN PATENT DOCUMENTS

EP    2361648 A1    8/2011
EP    2364740 A1    9/2011
(Continued)

OTHER PUBLICATIONS

English Translation of Notice of Preliminary Rejection issued in Korean Patent Application No. 2017-7008774.
(Continued)

*Primary Examiner* — Jenna Zhang
(74) *Attorney, Agent, or Firm* — McDonnell Boehnen Hulbert & Berghoff LLP

(57) ABSTRACT

The present invention relates to a signal delaying assembly for a medicament delivery device, said assembly comprising a delay female member containing a fluid, a delay male member having at least one passage, a delay unit connected to the delay female member or to the delay male member, wherein a relative movement between the male member and the female member and towards each other causes the transfer of said fluid from said female member through the at least one passage for slowing said movement, characterized in that the delay unit is releasably connected to a signal generating assembly for delaying at least one feedback signal.

13 Claims, 16 Drawing Sheets

(51) Int. Cl.
*A61M 5/50* (2006.01)
*A61M 5/32* (2006.01)
*A61M 5/31* (2006.01)

(52) U.S. Cl.
CPC ........ *A61M 5/3271* (2013.01); *A61M 5/5086* (2013.01); *A61M 5/3204* (2013.01); *A61M 2005/206* (2013.01); *A61M 2005/2013* (2013.01); *A61M 2005/3143* (2013.01); *A61M 2005/3247* (2013.01); *A61M 2005/3267* (2013.01); *A61M 2205/581* (2013.01); *A61M 2205/582* (2013.01); *A61M 2205/583* (2013.01)

(58) Field of Classification Search
CPC ...... A61M 2005/206; A61M 2205/583; A61M 2205/582; A61M 2205/581
See application file for complete search history.

(56) References Cited

U.S. PATENT DOCUMENTS

| | | | | |
|---|---|---|---|---|
| 7,901,377 | B1 * | 3/2011 | Harrison | A61M 5/2033 604/156 |
| 7,976,514 | B2 * | 7/2011 | Abry | A61M 5/326 604/110 |
| 9,486,582 | B2 | 11/2016 | Abry et al. | |
| 2012/0323177 | A1 * | 12/2012 | Adams | A61M 5/2033 604/135 |
| 2013/0041323 | A1 * | 2/2013 | Daniel | A61M 5/2033 604/189 |
| 2013/0218093 | A1 * | 8/2013 | Markussen | A61M 5/001 604/198 |
| 2014/0330214 | A1 * | 11/2014 | Olson | A61M 5/20 604/189 |
| 2015/0209517 | A1 * | 7/2015 | Brunnberg | A61M 5/2033 604/198 |
| 2015/0235571 | A1 * | 8/2015 | Alexandersson | A61M 5/31501 434/262 |
| 2017/0087304 | A1 * | 3/2017 | Gylleby | A61M 5/2033 |
| 2017/0165428 | A1 * | 6/2017 | Sall | A61M 5/2033 |

FOREIGN PATENT DOCUMENTS

| | | | | |
|---|---|---|---|---|
| FR | 2905273 | A1 | 3/2008 | |
| WO | 2005115506 | A1 | 12/2005 | |
| WO | 2005115516 | A1 | 12/2005 | |
| WO | WO-2005115516 | A1 * | 12/2005 | .......... A61M 5/2033 |
| WO | 2010049239 | A1 | 5/2010 | |
| WO | 2011123024 | A1 | 10/2011 | |
| WO | WO-2011123024 | A1 * | 10/2011 | .......... A61M 5/2033 |
| WO | 2013178512 | A1 | 12/2013 | |
| WO | WO 2013178512 | A1 * | 12/2013 | .......... A61M 5/2033 |
| WO | WO-2013178512 | A1 * | 12/2013 | .......... A61M 5/2033 |

OTHER PUBLICATIONS

Search Report issued in Swedish Patent Application No. 1451017-6 dated Mar. 24, 2015.
Search Report issued in Taiwanese Patent Application No. 104127693 dated Oct. 14, 2016.
Notice of Grounds of Rejection issued in Japanese Patent Application No. 2017-511916 dated Mar. 27, 2018.

* cited by examiner

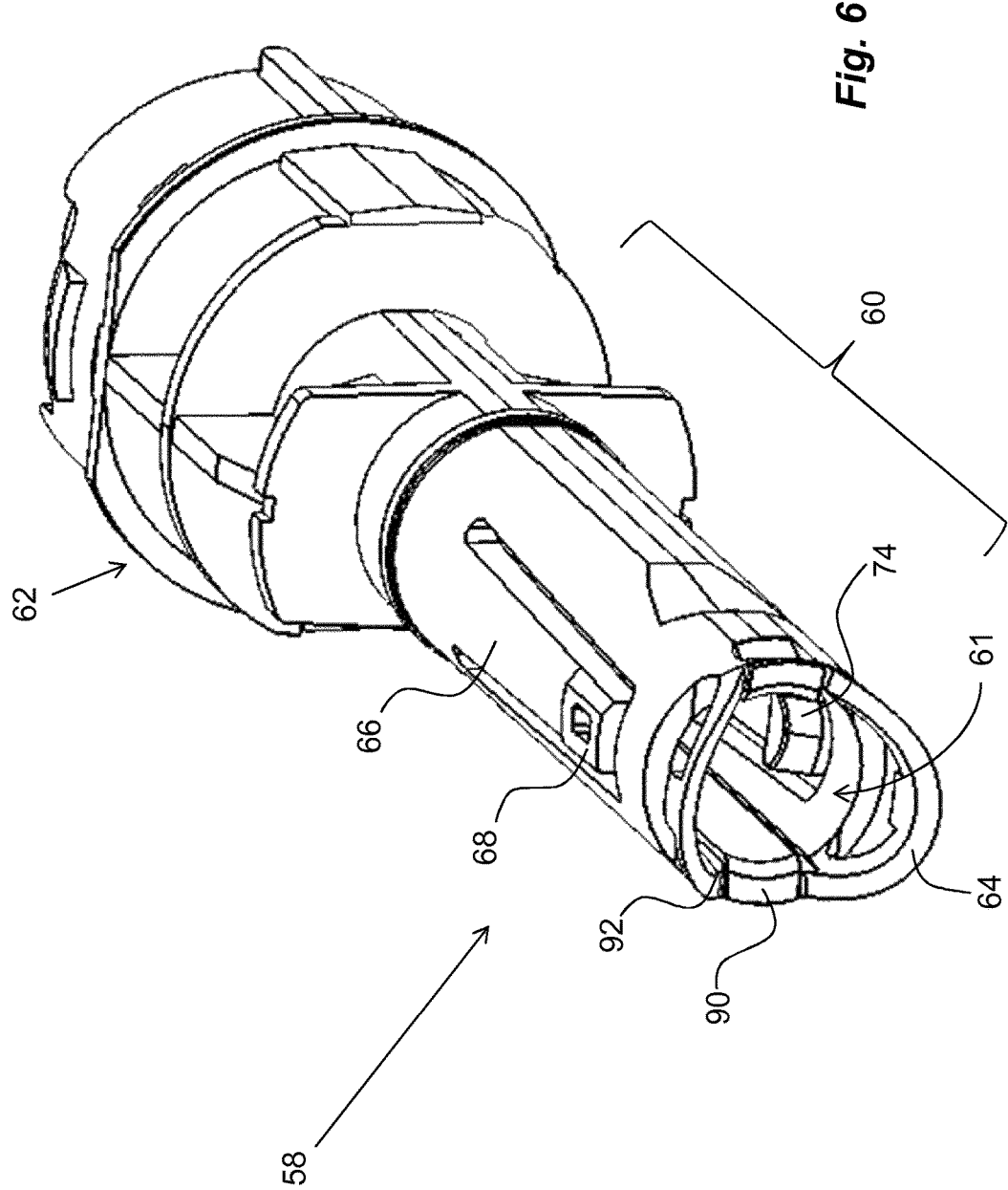

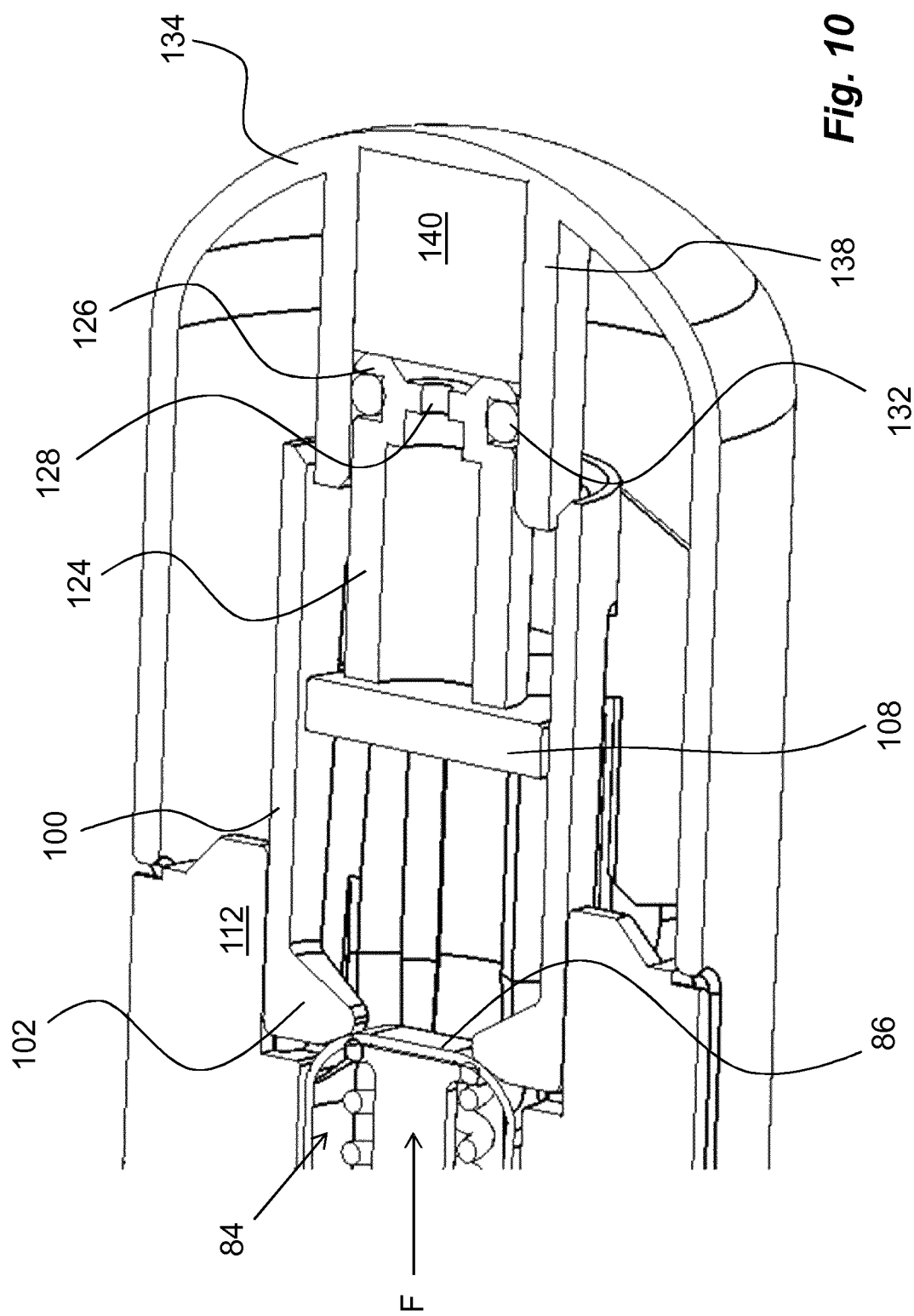

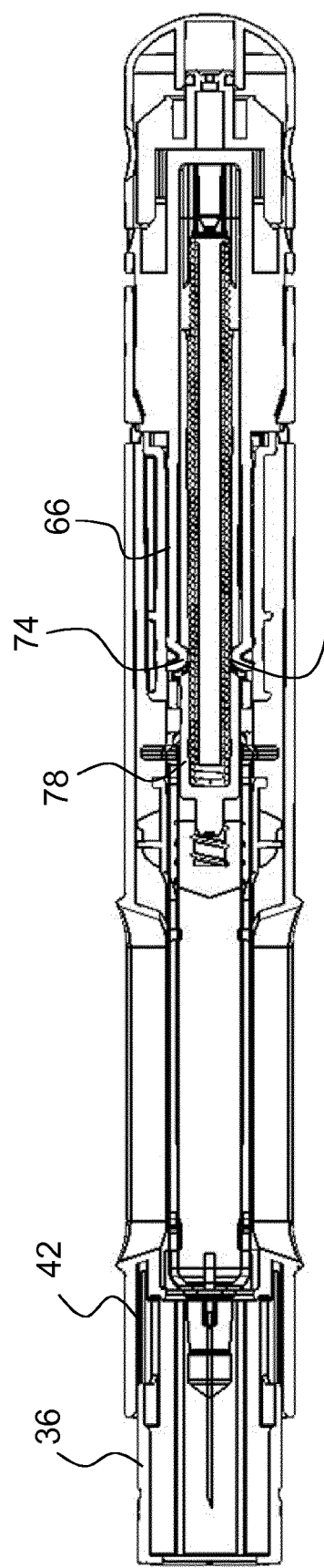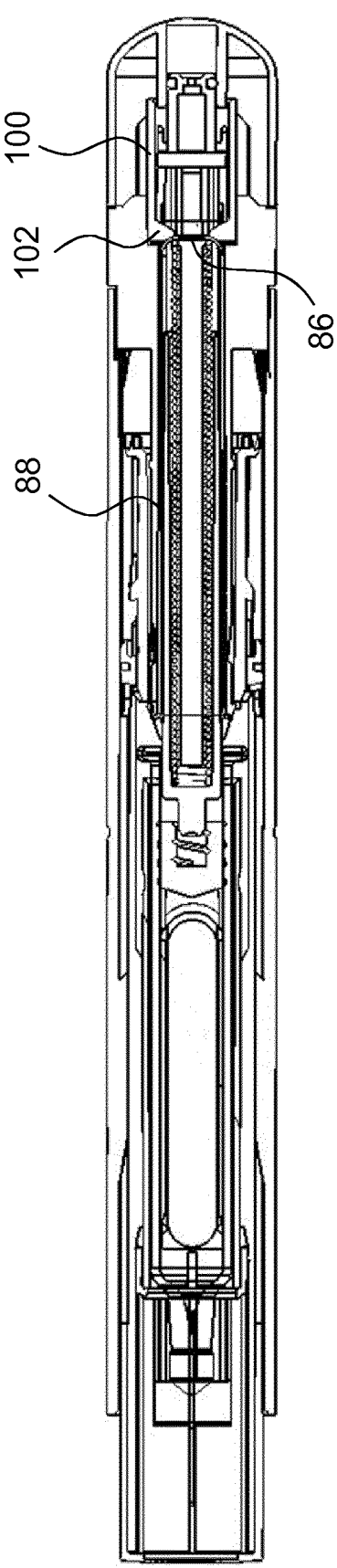

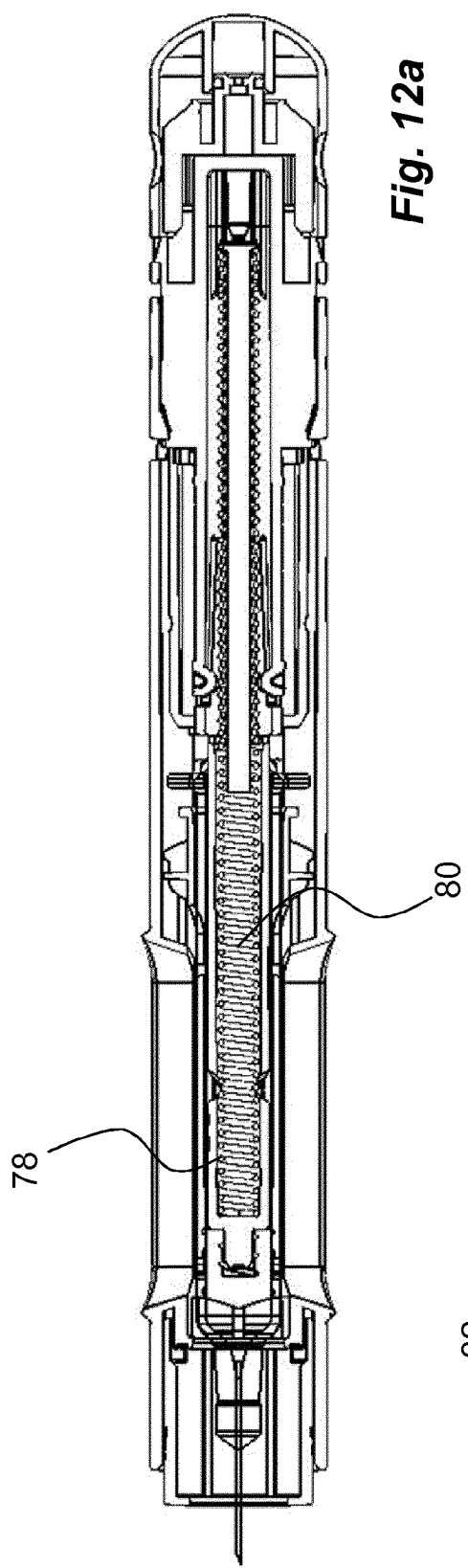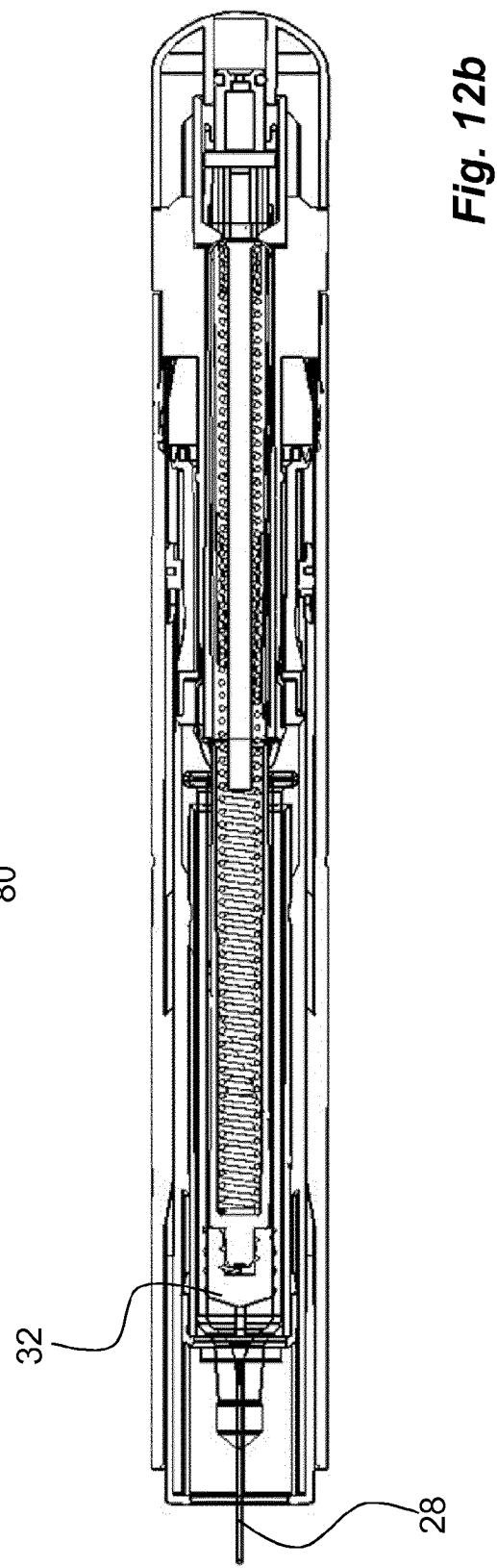

SIGNAL DELAYING ASSEMBLY FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2015/068951 filed Aug. 18, 2015, which claims priority to Swedish Patent Application No. 1451017-6 filed Sep. 1, 2014. The entire disclosure contents of these applications are herewith incorporated by reference into the present application.

TECHNICAL AREA

The present invention relates to a signal delaying assembly for a medicament delivery device capable of delaying at least one feedback signal that provides information to a user that a certain functional sequence has been performed.

BACKGROUND OF INVENTION

Many medicament delivery devices are developed for self-administration, i.e. a user performs the medicament delivery by her-, or himself. This requires a medicament delivery device which is reliable, accurate, safe and easy to use. In order to meet these requirements, the risk of human errors must be minimized, the number of actions that need to be performed in order to receive a dose have to be reduced and the device must be intuitive to use. Thus, in order to minimize the risk of human errors, it is desirable to have a device that accurately provides a user with confirmation that he/she has received a complete dose of medicament.

Medicament delivery devices such as injection devices providing automatic or manual delivery member insertion, automatic injection of a medicament, automatic delivery member retraction or automatic covering of the delivery member are known in the art. Although these injection devices have a number of advantages, there is always room for improvement. For example, a device that provides both a complete delivery of medicament and release of a member that produces a reliable audible and/or tactile and/or visible confirmation to the user that the delivery has been completed, has hitherto required extremely tight tolerances in manufacturing.

Such a release of a member for producing a reliable end-of-dose confirmation to the user is disclosed in WO2011043714A1. The releasing action is accomplished by disengaging a holding member from a plunger rod once the plunger rod has terminated its movement for delivering the medicament. The termination of the plunger rod displacement and the disengaging of the plunger rod from the holding member must occur simultaneously if both a complete delivery of a medicament and a release of the holding member which produces the reliable audible and/or tactile and/or visible confirmation to the user that the delivery has been completed are to be accomplished.

Thus, in WO2011043714A1 there is only one mechanical position that is used to activate the release of the second activation member at the point where it is expected that the plunger displacement will terminate. The precision of the timing of the termination of plunger displacement and disengagement of the plunger from the second activation member relies on the manufacturing and assembly dimensions of the parts of the device and thus the tolerances play an important role in the proper functioning of the device.

Document EP 2 705 861 discloses a medicament delivery device comprising a so called controlling means for producing sensory information, e.g. that an injection sequence has been completed. The device is further arranged with so called temporizing means, i.e. a delay mechanism that affects the controlling means such that the generation of the information is delayed, in order to ascertain that a sequence is really completed when the signal is produced such that the device can be removed.

The application of the controlling means as well as of the temporizing means is rather complicated, comprising a rotatable cog wheel having the rotational speed controlled and reduced, e.g. by grease. The cog wheel is operably connected to a sensory indicator via a ratchet rail on the controlling means and temporizing means assembly. The controlling means and temporizing means assembly are in a preloaded state before activation. When the device is used the controlling means and temporizing means assembly are released near the end of the injection sequence. The ratchet will move but the movement is slowed down by the cog wheel co-acting with the grease, thereby delaying the action of the sensory indicator.

As can be understood, there are a large number of components comprised in the solution that need to interact with each other in order to obtain the delayed signal. There is thus room for improvements in the technical area.

BRIEF DESCRIPTION OF INVENTION

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient.

The aim of the present invention is to remedy the drawbacks of the state of the art devices described. This aim is obtained by a signal delaying assembly for a medicament delivery device comprising the features of the independent patent claim. Preferable embodiments of the invention form the subject of the dependent patent claims.

According to a main aspect of the invention, the signal delaying assembly comprises a delay female member containing a fluid, a delay male member having at least one passage, a delay unit connected to the delay female member or to the delay male member, wherein a relative movement between the male member and the female member, and towards each other, causes a transfer of said fluid from said female member through the at least one passage for slowing said movement. The delay unit is releasably connected to a signal generating assembly of the medicament delivery device for delaying at least one feedback signal.

The signal delaying assembly further comprises a support element which is releasably connected to the delay unit such that the relative movement between the delay female member and the delay male member causes a relative movement between the delay unit and the support element causing the signal generating assembly to be released from the delay unit for generating the at least one feedback signal. Further, the delay unit is movably arranged in relation to the support element from a delaying position in which the delay unit is in contact with both the support element and with the signal generating assembly, to a released position in which the delay unit is disconnected from both the support element and the signal generating assembly.

According to one aspect of the invention, the delay unit comprises a flexible arm and a free end of the arm is arranged with an inwardly directed ledge. Accordingly, the delay unit is longitudinally movable in relation to the support element from a delaying position in which the flexible arm is in contact with the support element and in which the inwardly directed ledge is in contact with the signal generating assembly, to a released position in which the flexible arm is disconnected from the support element and in which the inwardly directed ledge is disconnected from the signal generating assembly by a radial movement of the flexible arm in relation to the support element.

According to another aspect of the invention, the signal generating assembly comprises a signal generating member and a force element. The force element is arranged tensioned between said signal generating member and a plunger rod for moving the plunger rod and the signal generating member respectively. The signal generating member is releasably connected to a holding unit of the medicament delivery device, wherein a pre-determined proximal and longitudinal movement of the plunger rod in relation to the holding unit allows the signal generating member to be released such that the force element forces the signal generating member to move distally in relation to the holding unit. The holding unit is a component of the medicament delivery device.

According to a further aspect of the invention, the delay unit is in contact with the signal generating member such that the movement of the signal generating member causes the delay unit to move from the delaying position to the released position. When the delay unit is in the released position, it disconnects from both the support element and the signal generating member whereby the signal generating member is forced distally by the force element in relation to the support element and the delay unit. The distal movement of the signal generating member causes an interaction between the signal generating member and a relatively fixed surface such that the at least one feedback signal is generated. Preferably, the relatively fixed surface may be a part of the holding unit. The use of a fixed surface on which the signal generating member impacts will provide both a sound that the user may hear as well as a vibrating sensation in the device. The creation of both a sound and vibration will enhance the possibility of the user obtaining the information that the device may be removed. The signal generating member is released when said plunger rod has moved a certain pre-determined distance. Thus the signal generating member is released during the movement of the plunger rod when performing the dose delivery sequence. Preferably the signal generating member is released near the end of the dose delivery sequence while the plunger rod is still moving.

According to one feasible solution, the signal generating member may comprise a U-shaped bracket arranged with its base in contact with said signal delaying assembly and wherein the force element acts on the signal generating member. Preferably the U-shaped base of the signal generating member is in contact with the inwardly directed ledge of the arm of the delay unit. Thus, the signal generating member is first released from a relatively fixed surface, which may be a part of the holding unit, causing the signal generating member to act on the signal delaying assembly. After a certain time period during transfer of the fluid, the signal generating member is released from the delay unit and will then create the desired signal.

According to another aspect of the invention, said interaction is an audible and/or tactile impact.

According to a further aspect of the invention, the delay unit comprises a visual indicia, such that when the delay unit is in the released position, said indicia is visible. The housing of the medicament delivery device is preferably arranged with windows through which the visual indicia may be visible to a user when the delay unit is in the released position. This provides the user with further information that the dose delivery sequence has ended and that it is safe to remove the device. Also, the visual indicia may also indicate that the device has been used. This reduces the risk that a user attempts to use a device that has already been spent.

According to a one more aspect of the invention, the fluid is a highly viscous fluid. Preferably, the fluid that is used comprises grease. Since grease has a high viscosity, it will require some force to squeeze the grease through the passage of the signal delaying assembly. Also grease will provide the possibility to alter the delaying time by using grease with different viscosity. It is however to be understood that other fluids that display the right properties may be used as well.

According to a further aspect of the invention, the holding unit is fixedly connected to a housing of the medicament delivery device and the support element is an integral part of the holding unit or a component that is fixedly connected to the holding unit.

It is also an object of the invention to obtain an enhanced medicament delivery device comprising all the preceding aspects and objects of the signal delaying assembly.

The medicament delivery device comprises a housing, which housing is capable of containing a medicament container, wherein the medicament container may accommodate a medicament delivery member. The medicament delivery member may either be attached to or made integral with the medicament container or may be a connectable delivery member for delivery of a medicament. The connection elements may be of different type, like threads, bayonet connections or luer connections, for example.

The medicament delivery device may further comprise a plunger rod operably arranged to move a stopper of the medicament container for expelling a dose of medicament through the medicament delivery member, and force element operably connected to the plunger rod. The force element may be of a number of different designs that are capable of exerting a force on the plunger rod. Typical force elements are springs of different types such as compression spiral springs, clock springs, torsion springs, gas springs, etc.

The delay unit is releasably connected to a signal generating assembly of the medicament delivery device for delaying at least one feedback signal.

The signal generating assembly of the medicament delivery device is configured to provide the at least one feedback signal when a dose has been delivered informing a user that a dose delivery sequence has been performed and that it is safe to remove the device. Without a signal generating assembly, the user will not know for certain when the delivery sequence has come to an end, and will have to guess, or estimate the time elapsed from the point of activating the device. Due to differences between devices regarding friction between components, force available from the force element etc., the time required for the delivery sequence may vary, which makes the time estimation more difficult for the user.

Thus, the medicament delivery device is further arranged with the signal delaying assembly which is operably connected to the signal generating assembly for delaying the generation of said at least one feedback signal. This ensures that the dose delivery sequence has been completely performed before the device is removed from the dose delivery site. Thereby, any residual quantities of medicament, that may remain in the medicament container due to e.g. the elasticity of the stopper, have safely been delivered.

According to a preferred solution, the medicament delivery device may be provided with the signal delaying assembly according to the aspects mentioned above. The transfer of the highly viscous fluid through the at least one passage creates a retarding action, whereby the movement of the elements that are to create the signal is slowed down so that it is ensured that the dose delivery sequence is definitely ended before the signal generating assembly is activated.

This solution provides a robust design with few components.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
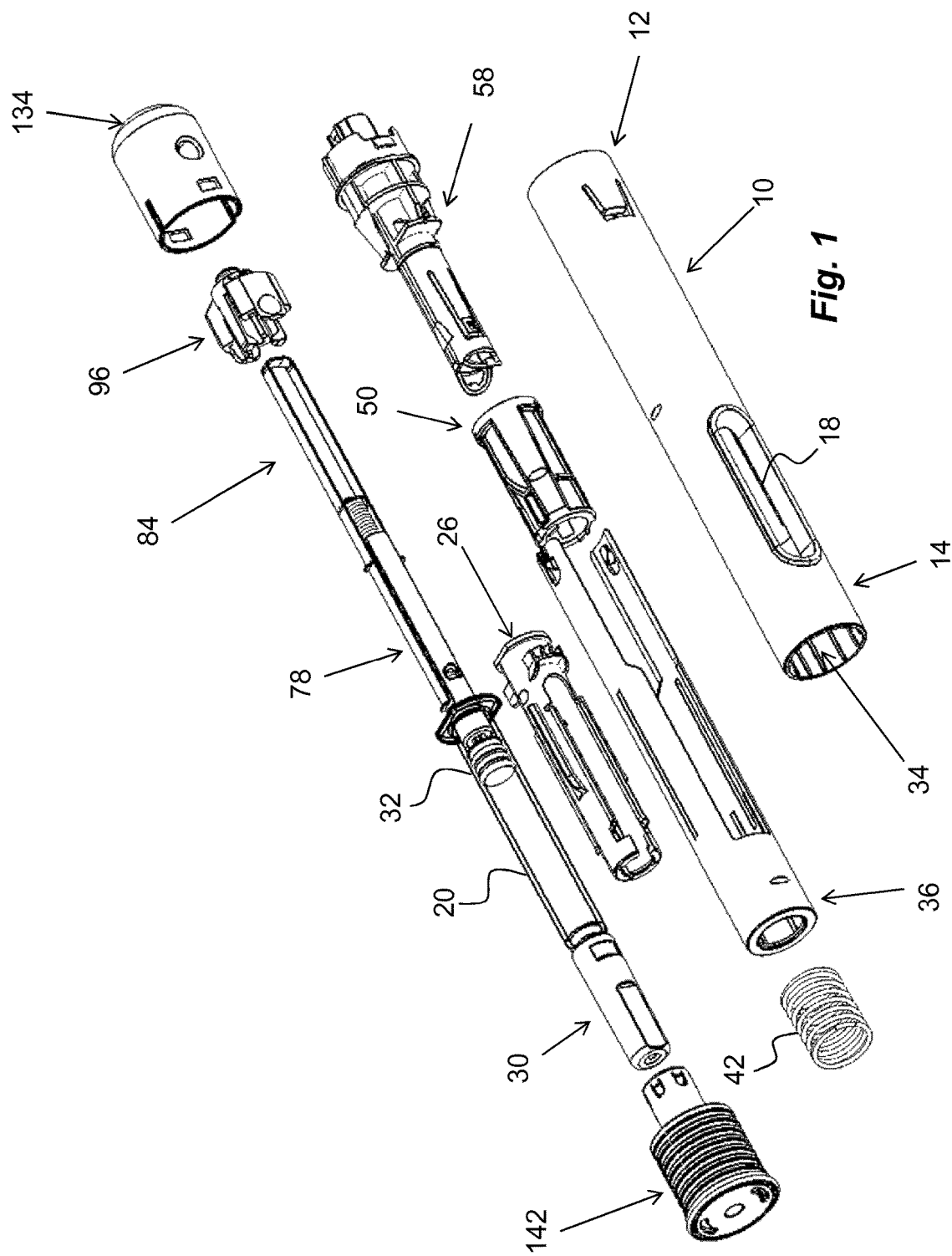
FIG. 1 is an exploded view of a medicament delivery device comprising the present invention.

An example of a signal delaying assembly for a medicament delivery device and an example of the medicament delivery device will be described.

The signal delaying assembly for a medicament delivery device shown in the drawings comprises a delay female member 138 containing a fluid 140, a delay male member 124 having at least one passage 128, FIG. 10, and a delay unit 96 (FIG. 9) which, in the exemplary embodiment is integral with the delay male member. In an alternative embodiment, the delay unit is instead integral with the delay female member, such that the delay female member is movable together with the delay unit. The delay unit 96 is releasably connected to a signal generating assembly of the medicament delivery device which generates at least one feedback signal indicating that a dose of medicament has been completely delivered. The male and the female members are configured to move towards each other such that a relative movement between the male member and the female member causes the transfer of said fluid from said female member through the at least one passage. The fluid is a highly viscous fluid and the at least one passage is configured such that the transfer of fluid is slow and thus the movement between the male and the female member i.e. the movement the delay unit and the delay male member relative to the delay female member is slowed, damped or delayed. When the fluid has been transferred, the signal generating assembly is released from the delay unit, producing a signal delayed by the signal delaying assembly.

Figure 8:
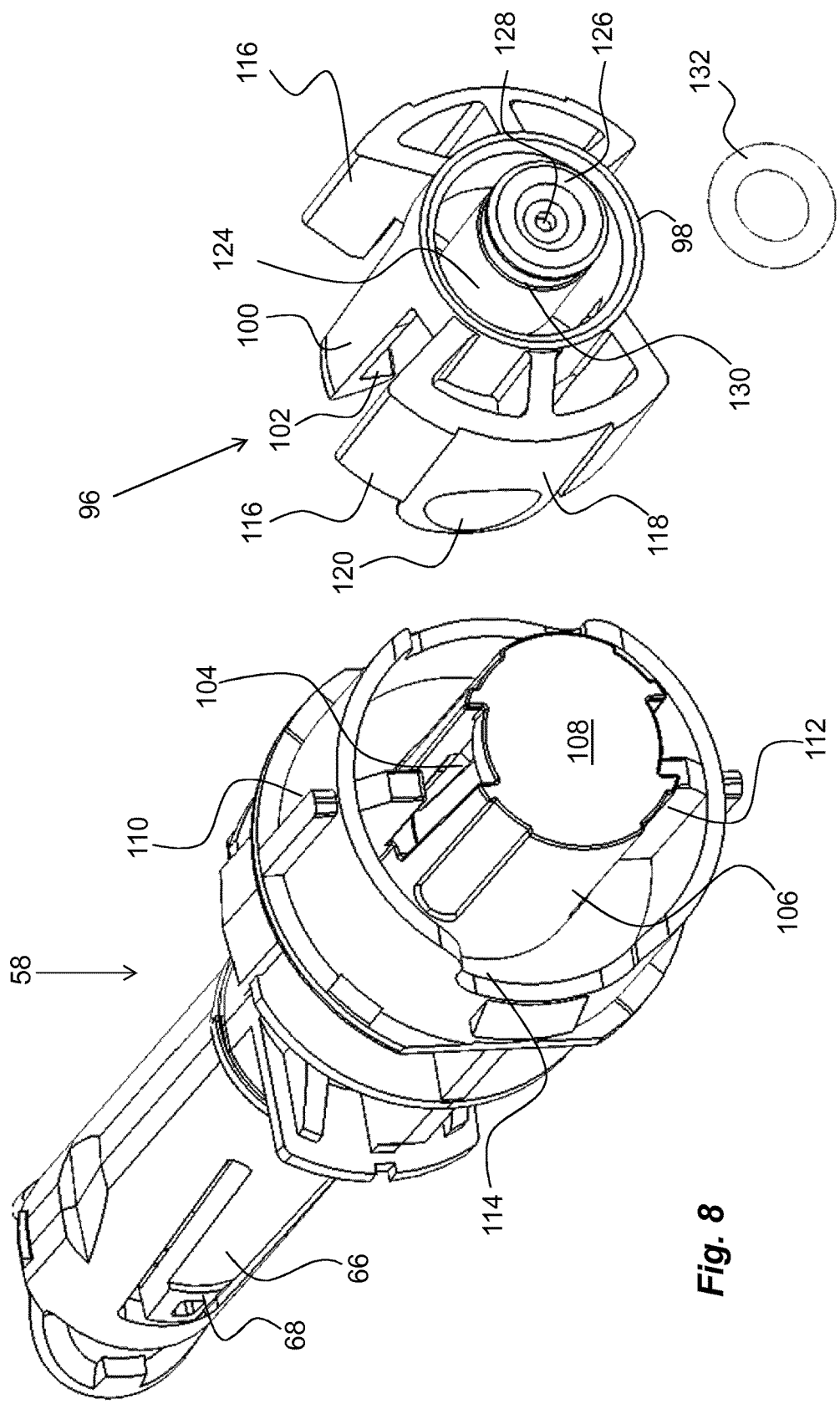

The signal delaying assembly further comprises a support element 112 which is releasably connected to the delay unit 96, FIG. 8, such that the relative movement between the delay female member and the delay male member causes a relative movement between the delay unit 96 and the support element 112 causing the signal generating assembly to be released from the delay unit for generating the at least one feedback signal. Further, the delay unit 96 is movably arranged in relation to the support element 112 from a delaying position in which the delay unit is in contact with the support element and with the signal generating assembly, to a released position in which the delay unit is disconnected from both the support element and the signal generating assembly.

Figures 3A, 3B:
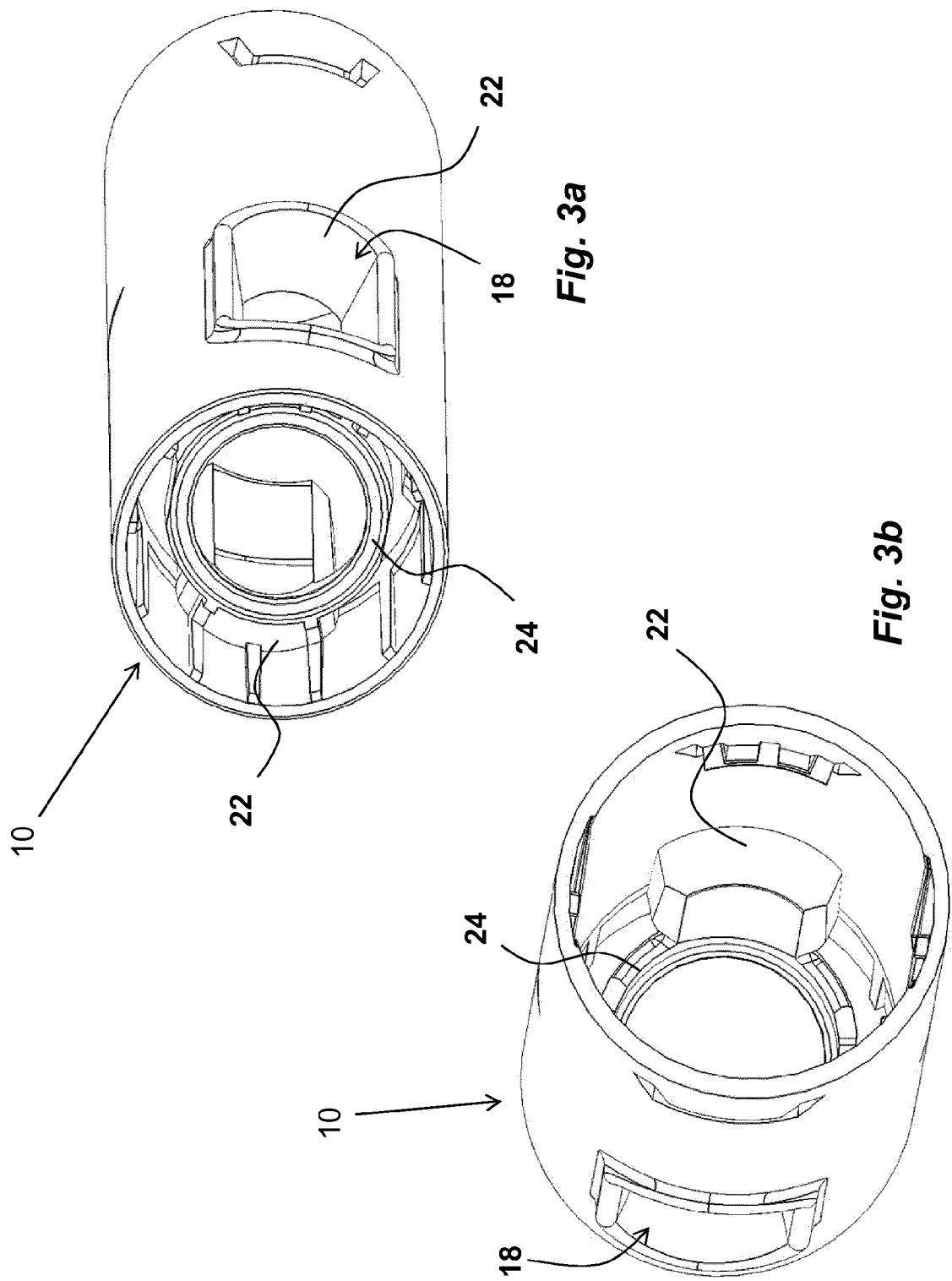

The medicament delivery device shown in the drawings comprises a housing which in the present embodiment is divided in two parts for assembly purposes. A first part is generally tubular elongated proximal housing 10 having a distal end 12 and a proximal end 14, and a second part is a distal housing 134 having the form of an end cap that is attachable to a distal end of the proximal housing 10 by suitable fastening elements. It is obvious that the two parts are fixed to each other, i.e. the housing of the device may be seen as one component. The proximal housing 10 is further arranged with windows or openings 18, FIGS. 1 and 3, through which a medicament container 20 can be viewed. Each opening 18 is arranged with an inwardly directed circumferential ledge 22, FIG. 3. A ring-shaped support element 24 is further attached to the ledges 22 of the openings 18. The device further comprises a medicament container holder 26 having a generally tubular shape, FIG. 1. The medicament container holder 26 is arranged to be supported in the generally radial direction by the ledges 22 of the openings 18 and in the generally longitudinal direction by the ring-shaped support element 24.

Figure 2:
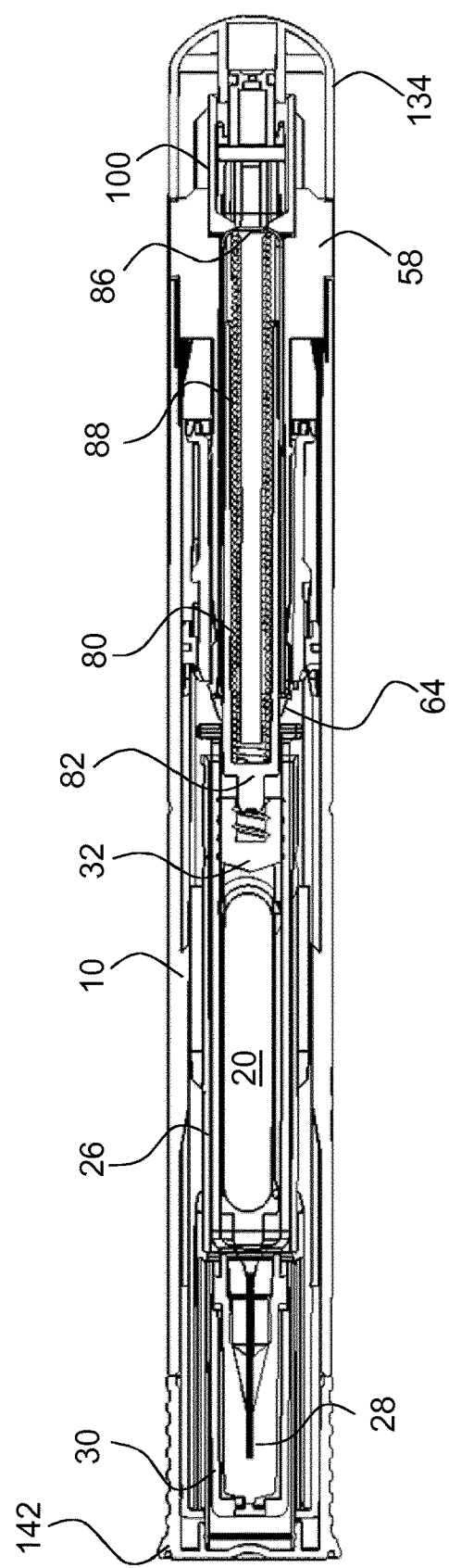
FIG. 2 is a cross-sectional view of the device of FIG. 1, FIGS. 3-9 are detailed views of components comprised in the device of FIG. 1, and FIGS. 10-16 are detailed views, some in cross-section, of functional states of the device of FIG. 1.

The medicament container holder 26 is arranged to accommodate the medicament container 20, where the medicament container 20 has a proximal end on which a medicament delivery member 28, FIG. 2, is arranged, either made integral or connectable to the medicament container 20. The medicament delivery member 28 is preferably protected before use by a medicament delivery member shield 30 that in the embodiment shown is a so called rigid needle shield or RNS. It is however to be understood that other types of medicament delivery member shields may be used in order to obtain the desired protection of the medicament delivery member. The medicament container 20 is further arranged with a movable stopper 32, FIG. 2.

Figure 4:
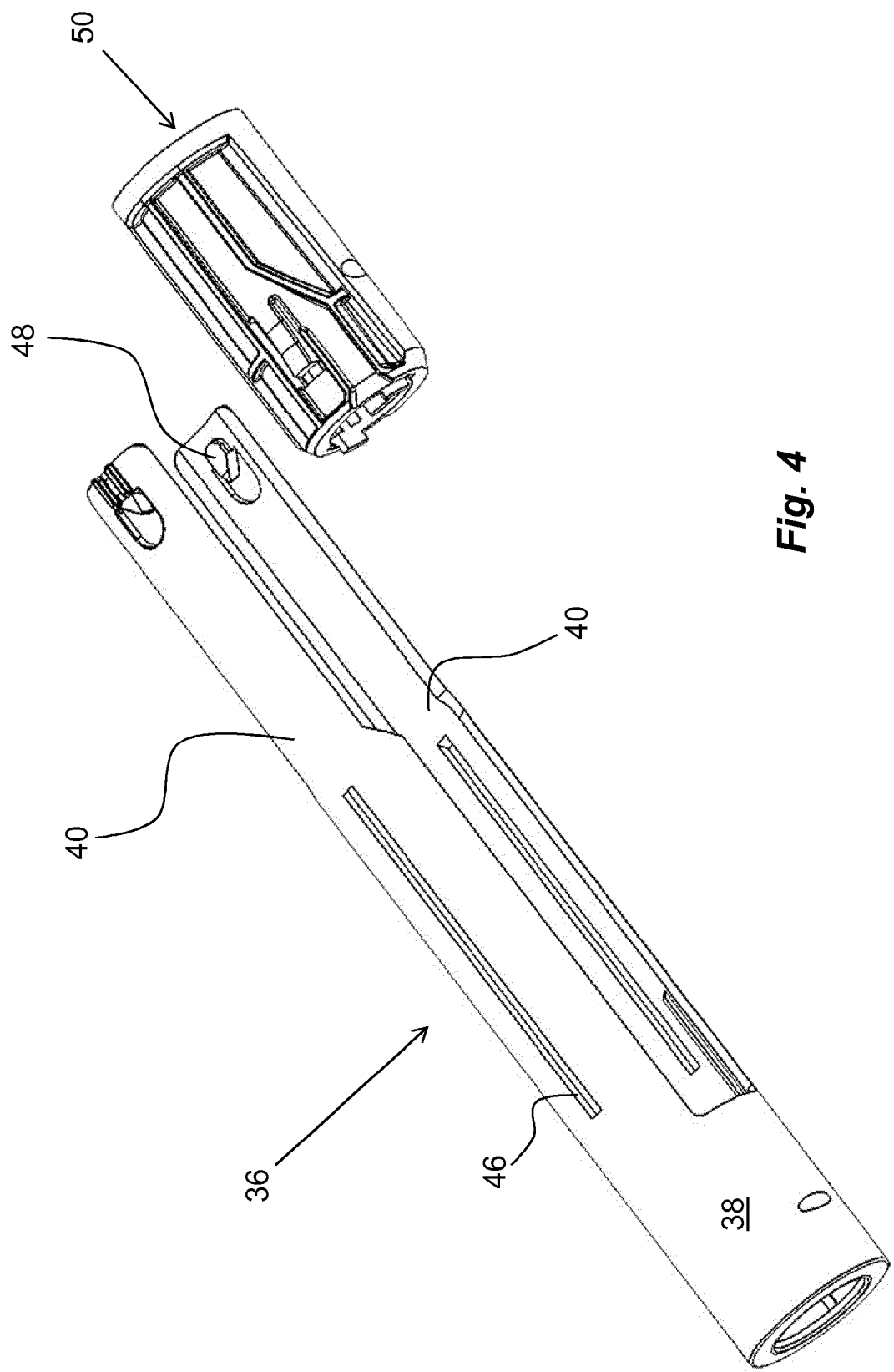

The proximal end of the proximal housing is arranged with a central passage 34, FIG. 1, through which a generally tubular medicament delivery member guard 36 extends, FIGS. 1 and 4. The medicament delivery member guard 36 is arranged slidable in the housing 10. The medicament delivery member guard 36 comprises a proximal tubular 38 part and two distally directed arms 40 extending from the tubular part 38. A medicament delivery member guard spring 42 is arranged between a distally directed circumferential wall part of the medicament delivery member guard 36 and a proximally directed circumferential surface of the housing. The arms 40 are arranged slidable along the medicament container holder 26 and are guided by elongated ledges on the outer surface of the medicament container holder 26 fitting into elongated grooves 46, FIG. 4, in the arms 40. At the distal end of the arms 40, inwardly directed protrusions 48 are arranged, FIG. 4. The protrusions are arranged to operably interact with a rotator 50, FIGS. 4 and 5, in turn positioned distally of the medicament container 20.

Figure 5B:
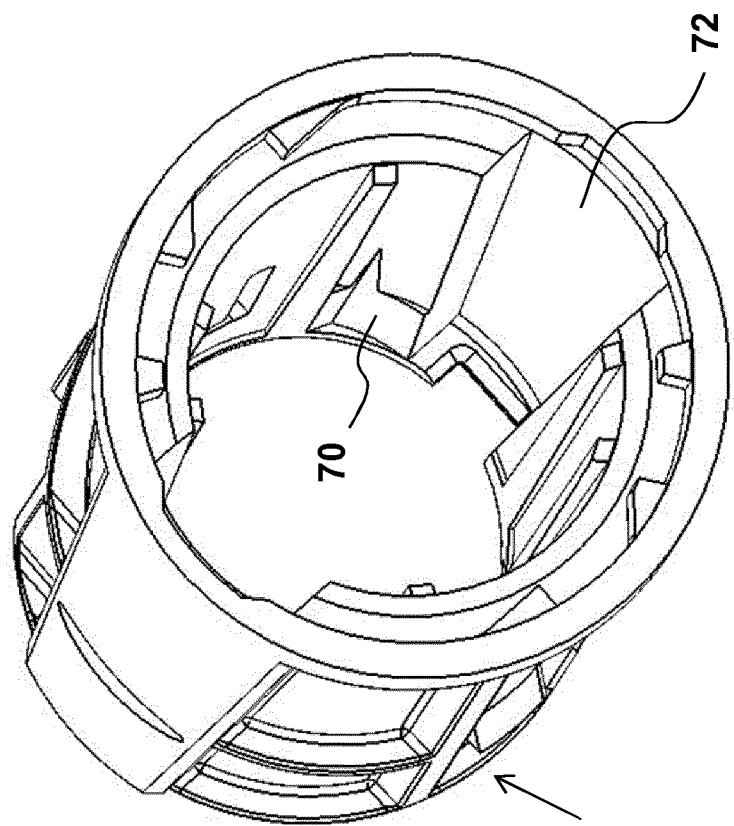
Figure 5A:
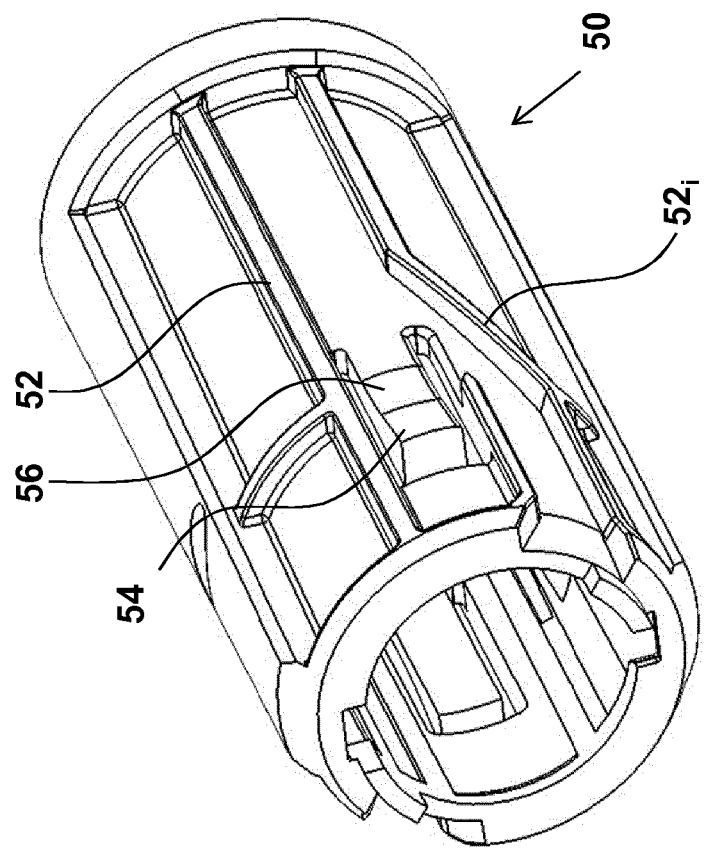

The rotator 50 has a generally tubular shape and is arranged with guide ridges 52 that are intended to cooperate with the protrusions 48 of the medicament delivery member guard 36 as will be described, wherein some sections $52_i$ of the guide ridges are inclined in relation to the longitudinal direction of the device, FIG. 5. The rotator 50 is further arranged with wedge-shaped protrusions 54 arranged on generally radially flexible tongues 56, positioned adjacent the guide ridges 52, which wedge-shaped protrusions 54 are intended to lock the medicament delivery member guard 36 after completed use of the device, as will be described.

A holding unit 58 is further operably arranged to the rotator 50. The holding unit 58, FIGS. 6 and 8, comprises a first proximal tubular section 60 having a diameter slightly smaller than the inner diameter of the rotator 50 and being provided with a central passage 61, FIG. 6. It further comprises a second section 62 arranged to fit into and to be attached to a distal part of the proximal housing 10. The first section 60 is further arranged with holding elements 64 that in the embodiment shown is in the form of arch-shaped elements extending in the proximal direction from a proximal end surface of the first section 60. The holding elements 64 are arranged to come in contact with and press on a distal end surface of the medicament container 20 when placed in the medicament container holder 26, FIG. 2. The holding unit is configured to be fixedly connected to the housing.

Further, the first section 60 is arranged with proximally extending arms 66 that are flexible in a generally radial direction. The free ends of the arms 66 have outwardly extending protrusions 68 that are to interact with inner surfaces of the rotator 50 as will be described. In that respect, the rotator 50 is arranged with support surfaces 70 as well as longitudinally extending recesses 72 adjacent the support surfaces 70 as seen in FIG. 5*b*, wherein the support surfaces 70 as well as the recesses 72 will interact with the outwardly extending protrusions 68, as will be described. Further the free ends of the arms 66 are arranged with inwardly extending protrusions 74, which protrusions 74 extend into the central passage 61 and are intended to interact with recesses 76 on a plunger rod 78, FIG. 7, which plunger rod 78 is to be placed inside the central passage of the holding unit 58. In that respect, the diameter of the plunger rod 78 is somewhat smaller than the diameter of the central passage 61.

Figure 7:
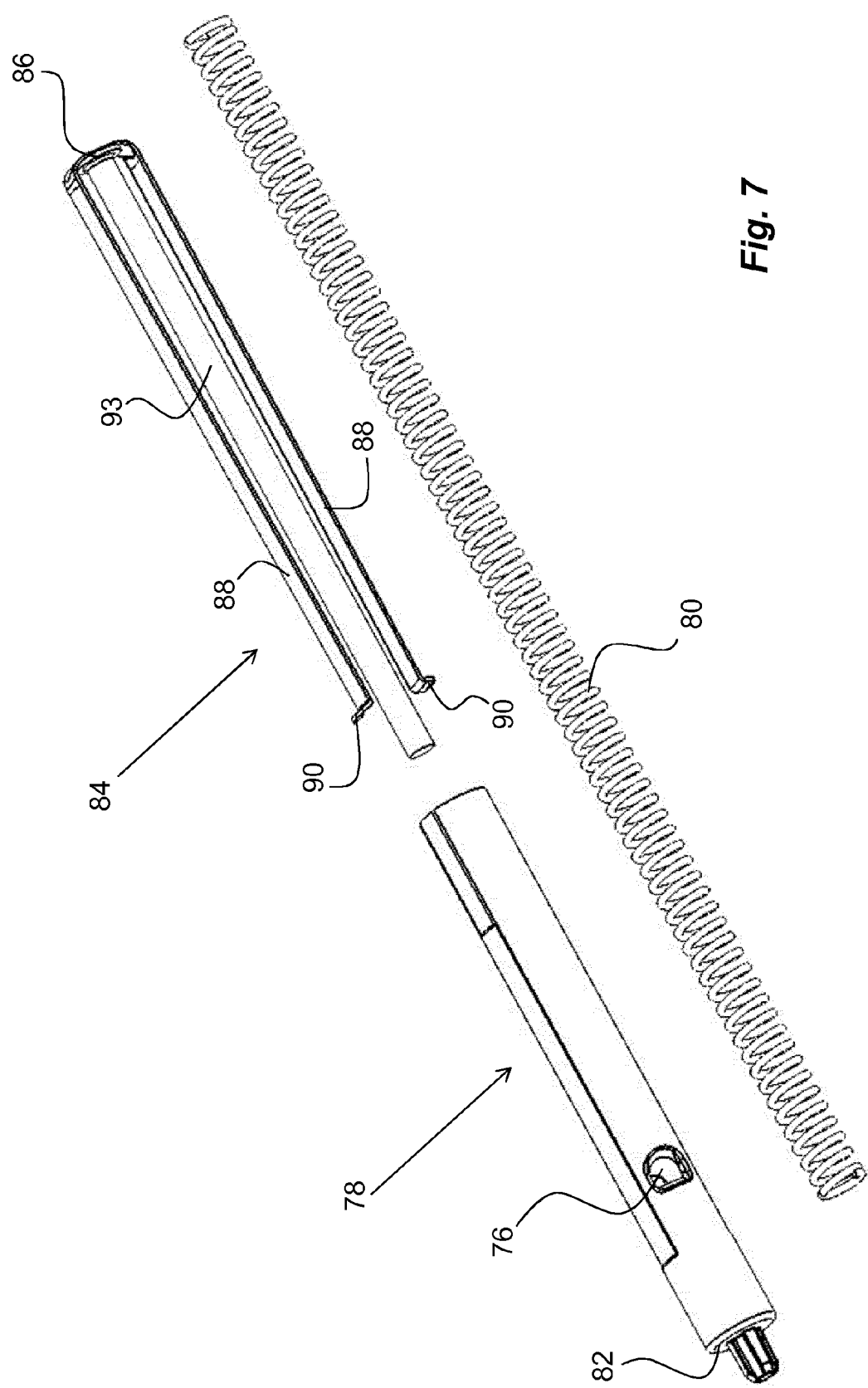

The signal generating assembly comprises a signal generating member 84 and a force element, FIG. 7. The force element 80 is arranged tensioned between said signal generating member and the plunger rod 78, FIGS. 2, 11*a*-12*b*, and is configured to move the plunger rod and the signal generating member, as will be described.

As seen in the FIGS. 2, 7 and 11*a*-12*b*, the force element 80 is a compression spring placed inside a cavity of the hollow plunger rod 78 and the signal generating member 84 is a generally U-shaped element having a base 86 and two arms 88. The force element is positioned with a proximal end thereof in contact with an end wall 82 of the plunger rod 78 and with a distal end in contact with the base 86 of the signal generating member 84, FIGS. 2, 7 and 11*a*-12*b*. The arms 88 of the signal generating member 84 are directed in the proximal direction along, and in contact with, the outer surface of the plunger rod 78, wherein the free ends of the arms 88 are arranged with generally radially outwardly directed ledges 90. These ledges 90 are arranged to be in contact with a proximally directed surface 92 surrounding the central passage 61 of the holding unit 58, FIG. 6. A spring guide rod 93, FIG. 7, is further arranged to a proximally directed surface of the base 86 and extending into the force element 80, for preventing buckling of the force element 80.

Figure 9:
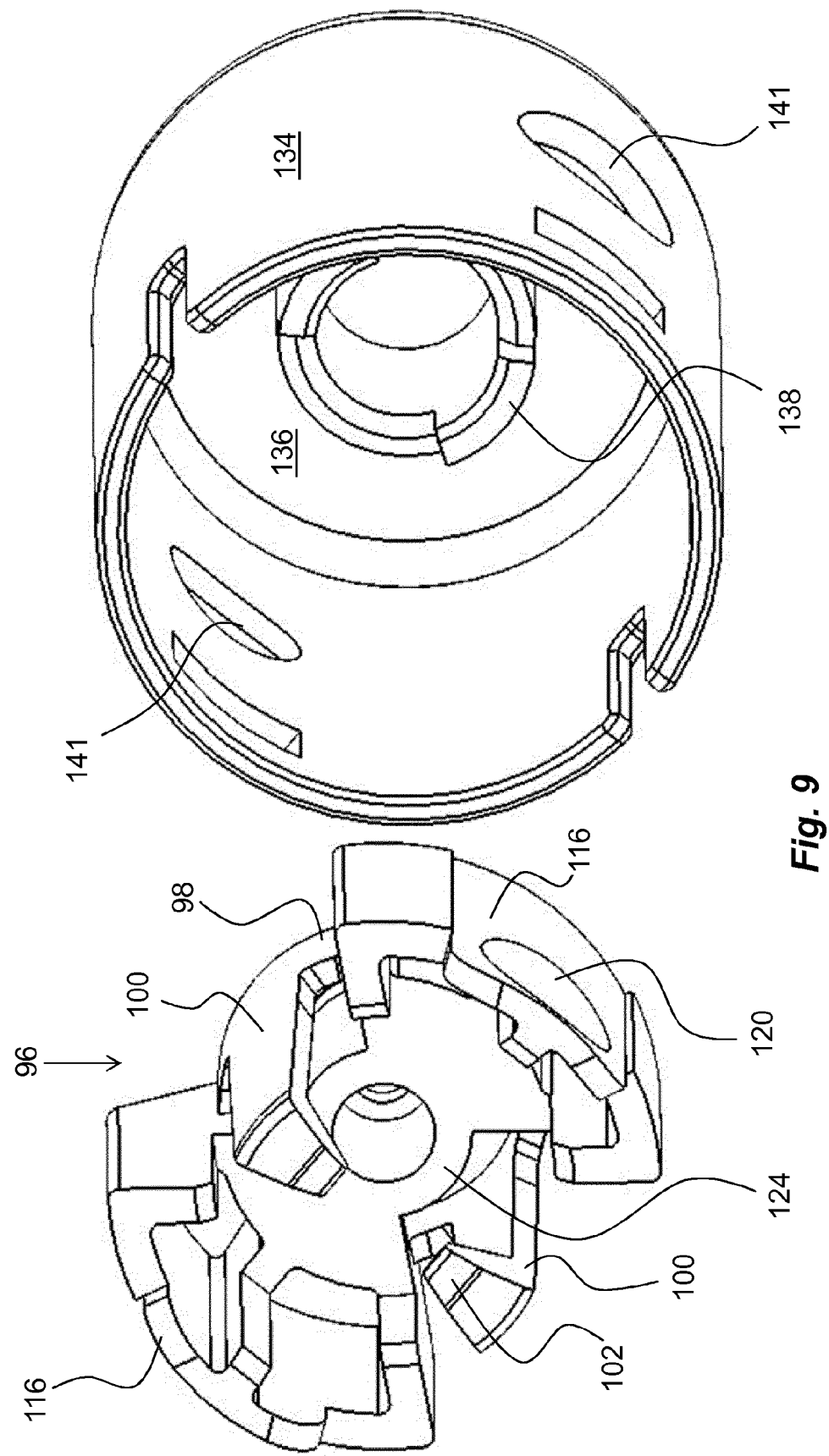

As shown in FIGS. 9 and 10, the distal housing 134 comprises an inner proximally directed surface 136 where the delay female member 138 is arranged. The delay female member 138 has a tubular shape and extends from the inner proximally directed surface 136 of the distal housing 134 towards the proximal direction. In an alternative embodiment, the delay male member is arranged at the proximally directed surface 136 and the delay female member is arranged at the delay unit 96.

As shown in the FIGS. 8 and 9, the delay unit 96 comprises flexible arms 100 and the free end of each arm is arranged with an inwardly directed ledge 102.

The generally proximally directed arms 100 are flexible in a generally radial direction and arranged to a main body 98 of the delay unit. The ledges 102 fit into longitudinal slots 104, FIG. 8, arranged on a generally tubular post 106 at the distal end of the holding unit 58. The post 106 is arranged with an end wall 108, the function of which will be described below. A generally tubular support member 110 is arranged coaxial with and surrounding the post 106, which tubular support member 110 is arranged to be in contact with the proximal housing 10 for supporting the holding unit 58.

The support elements 112 of the signal delaying assembly are arranged to the holding unit. As seen in FIGS. 8 and 10, the support elements 112 are integral with the holding unit, more specifically with the tubular support member 110: the support elements 112 are radially inwardly directed ledges that extend in the longitudinal direction and are positioned radially opposite to the slots 104 of the post 106. Further, the tubular support member 110 is arranged with cut-outs 114, the function of which will be described below. In an initial, non-activated, position of the device, as seen in FIG. 10, the arms 100 are in contact with the support elements 112, preventing movement of the arms in the generally radially outward direction. The inwardly directed ledges 102 of the arms 100 are further in contact with the distal end of the signal generating member 84, more specifically with the base 86 of the signal generating member.

The delay unit 96 further comprises visual indicia 120, such that when the delay unit is in the released position, said indicia is visible through the housing of the device. As seen in FIG. 8, the main body 98 of the delay unit 96 is further arranged with elements 116 that have a curved, outwardly directed, surface. The elements 116 are positioned generally in the same radial positions as the cut-outs 114 of the support member 110. The surfaces of the curved elements 116 are arranged with the visual indicia 120, such as symbols and/or certain colour indications, the function of which will be described below. Further, the main body 98 is arranged with generally radially inwardly directed bridges where the delay male member 124 is attached, extending in the distal direction. The delay male member 124 is arranged with an end wall 126 at its distal end where the passage 128 is arranged. At its distal end, the outer surface of the delay male member 124 is arranged with a circumferential groove 130, in which groove an elastic O-ring 132 can be fitted.

The diameter of the delay female member 138 is chosen such that the elastic O-ring 132 of the delay male member 124 is in sealing contact with the inner wall of the delay female member 138. In the initial, non-activated, position of the device, as seen in FIG. 10, there is a certain distance between the end wall 126 of the delay male member 124 and the proximal surface 136 of the distal housing 134. The distal housing 134 is further arranged with openings or windows 141, FIG. 9, that may align with the visual indicia 120 on the delay unit 96, the function of which will be described below.

Finally, the medicament delivery device is arranged with a protective cap 142, FIGS. 1 and 2, connectable to the proximal end thereof. The protective cap 142 extends with a tubular part 144 into the medicament delivery member guard 36 and surrounds the medicament delivery member shield 30. The inner surface of the tubular part 144 is arranged with grip elements 146 capable of gripping the medicament delivery member shield 30.

The signal delaying assembly together with the medicament delivery device is intended to function as follows. A medicament container 20 has been loaded into the medicament container holder 26 and placed in the housing of the device. The force element 80 is tensioned between the end wall 82 of the plunger rod 78 and the base 86 of the signal generating member 84 as seen in FIG. 2. The plunger rod 78 is held in position in relation to the holding unit 58 by the protrusions 74 of the arms 66 placed in the recesses 76 of the plunger rod 78. Further the arms 66 are prevented from being moved outwardly in the radial direction in that the outwardly directed protrusions 68 of the arms 66 are in contact with the support surfaces 70 of the rotator 50. Thus the force element is held in a pre-tensioned state.

Further the signal generating member 84 is prevented from being moved in the distal direction by the force of the force element 80 due to the ledges 90 resting on the surface 92 of the holding unit 58, FIG. 6. The arms 88 of the signal generating member 84 are further prevented from being moved in a generally radial direction by the plunger rod 78 being in contact with inner surfaces of the arms 88 as seen in FIG. 11b. Further, the ledges 102 of the arms 100 of the delay unit 96 are in contact with the distally directed surface of the base 86 of the signal generating member 84, and the arms 100 are prevented from moving in the generally radial direction by the support elements 112, as seen in FIG. 11b.

When delivered to a user, the proximal end of the medicament delivery device is provided with the protective cap 142 at its proximal end. When the device is to be used, the protective cap 142 is removed by pulling it in the proximal direction. This causes the grip elements 146 to grip into and remove the medicament delivery member shield 30 from the medicament delivery member 28. The medicament delivery member guard 36 is in its most proximal position, biased by the medicament delivery member guard spring 42, FIG. 11.

When the user presses the proximal end of the medicament delivery member guard 36 against a dose delivery site and when an injection needle is used as medicament delivery member 28, a penetration of the user's skin is performed. The medicament delivery member guard 36 moves in the distal direction in relation to the housing. This in turn causes the protrusions 48 of the medicament delivery member guard 36 to move along the guide ridges 52 of the rotator 50 such that the protrusions will come in contact with the inclined sections 52$_i$, which will cause the rotator 50 to turn around the longitudinal axis of the device.

The turning of the rotator 50 will cause the outwardly extending protrusions 68 of the holding unit 58 to move out of contact with the support surfaces 70 of the rotator 50 and into its recesses 72. The arms 66 of the holding unit 58 are now free to flex outwardly, whereby the inwardly directed protrusions 74 of the arms 66 are moved out of contact with the recesses 76 of the plunger rod 78.

The plunger rod 78 is now free to move in the proximal direction due to the force of the force element 80, wherein the proximal end of the plunger rod 78 acts on, and moves, the stopper 32 inside the medicament container 20 in the proximal direction such that a dose of medicament is expelled through the medicament delivery member 28, as seen in FIG. 12.

Figure 13:
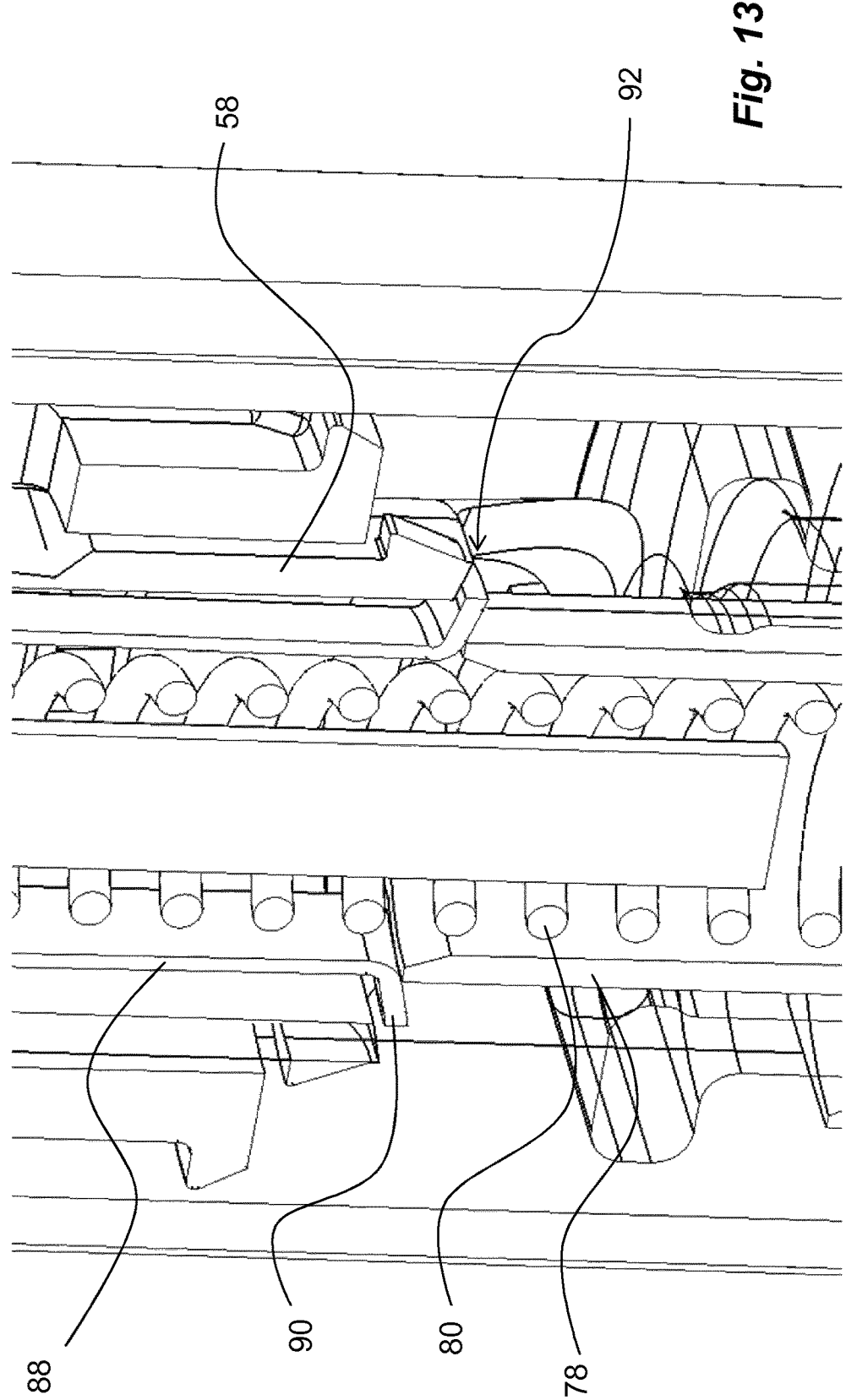

Depending on the tolerances, when the stopper 32 has been moved by the plunger rod 78 to the proximal end or to almost the proximal end inside the medicament container 20, the plunger rod 78 is moved out of contact with the arms 88 of the signal generating member 84 as seen in FIG. 13. The arms 88 of the signal generating member 84 are thus free to flex inwards such that the ledges 90 are moved out of contact with the surfaces 92 of the holding unit 58, and due to a remaining force in the force element 80, the signal generating member 84 will press with a distally directed force F on the ledges 102 of the arms 100 of the delay unit 96 of the signal delaying assembly FIG. 10. At the same time, the force element 80 will continue to urge the plunger rod in the proximal direction with a proximally directed force −F.

Figure 14:
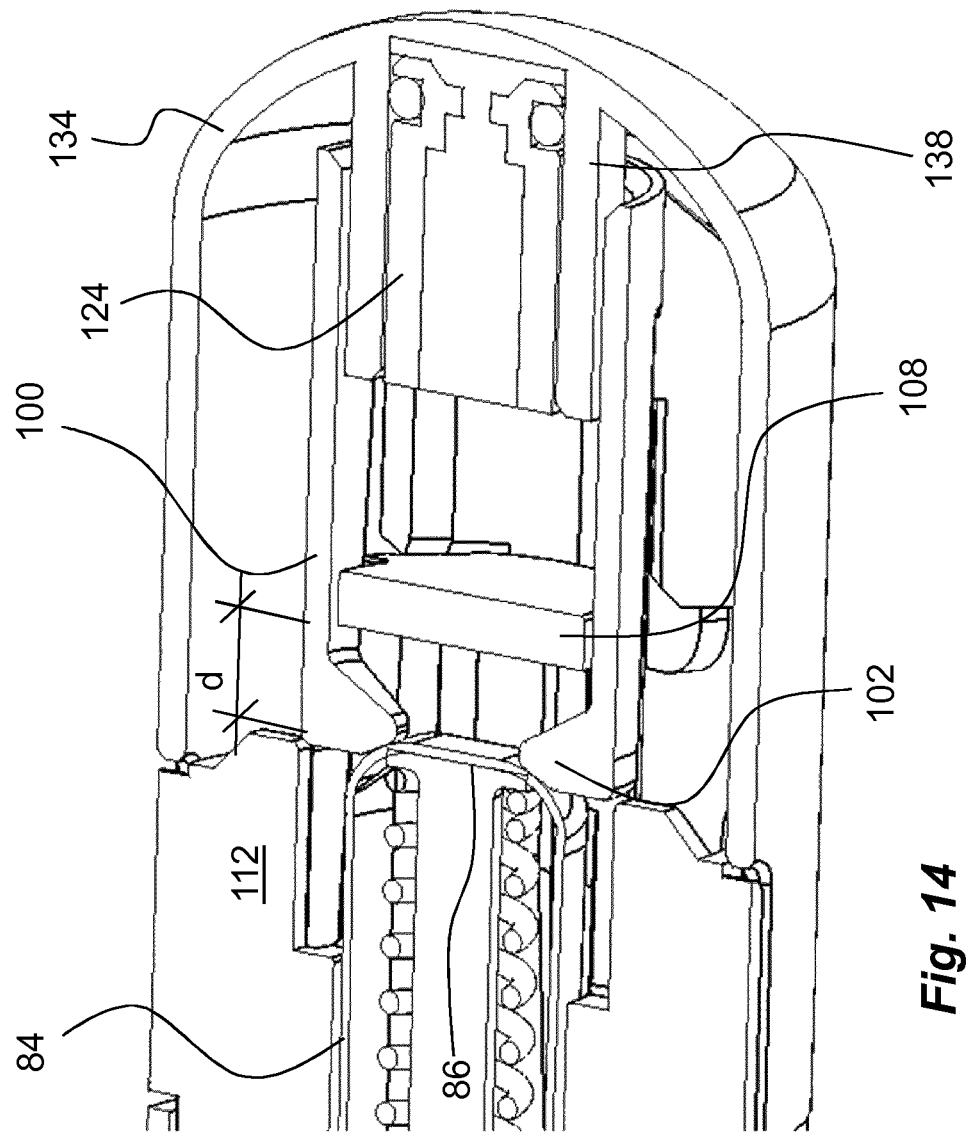

The delay unit 96 moves longitudinally in relation to the support elements 112 by the force F from the delaying position in which the flexible arms 100 are in contact with the support elements and in which the inwardly directed ledges 102 are in contact with the base 86 of the signal generating member 84, to the released position in which the flexible arms 100 are disconnected from the support elements and in which the inwardly directed ledges 102 are moved out of contact with the base 86 of the signal generating member 84 by a radial movement of the flexible arm in relation to the support elements as seen in FIG. 14. Thus, in the present embodiment the delay male member 124 is also moved in the distal direction inside the delay female member 138 and will exert a pressure on the fluid 140 contained therein. The pressure on the fluid will force it through the central passage 128, and since the passage is narrow and the fluid is highly viscous, the movement of both the signal generating member 84 and the delay unit 96, in the distal direction, is damped/slowed down. During the slow movement of the signal generating member 84, the stopper 32 is pressed or moved proximally to its end position, finishing the injection sequence.

Figure 15:
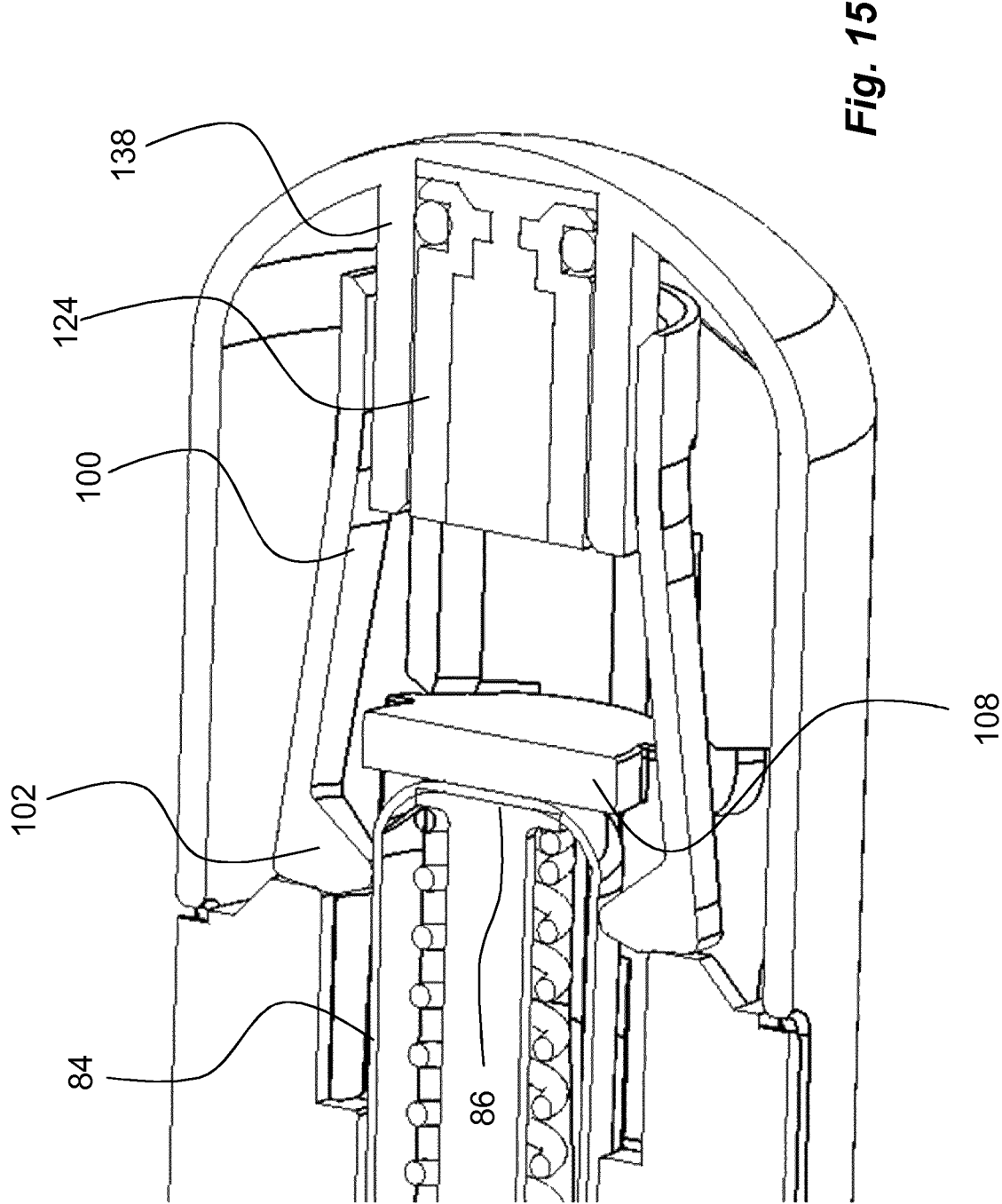

When the delay unit 96 has come to a certain position in relation to the holding unit 58 and the end wall 126 of the delay male member 124 has almost reached the proximal surface 136 of the distal housing 134, the arms 100 move out of contact with the support elements 112 as seen in FIG. 14, whereby the arms 100 flex outwards in a generally radial direction, FIG. 15. As seen in FIG. 14, a pre-determined distance d has been designed between the release point of the signal generating member and the proximally directed surface of the end wall 108 of the holding unit 58, which is a relatively fixed surface, i.e. longitudinally fixed relative to the movement of the signal generating member 84.

Figure 16:
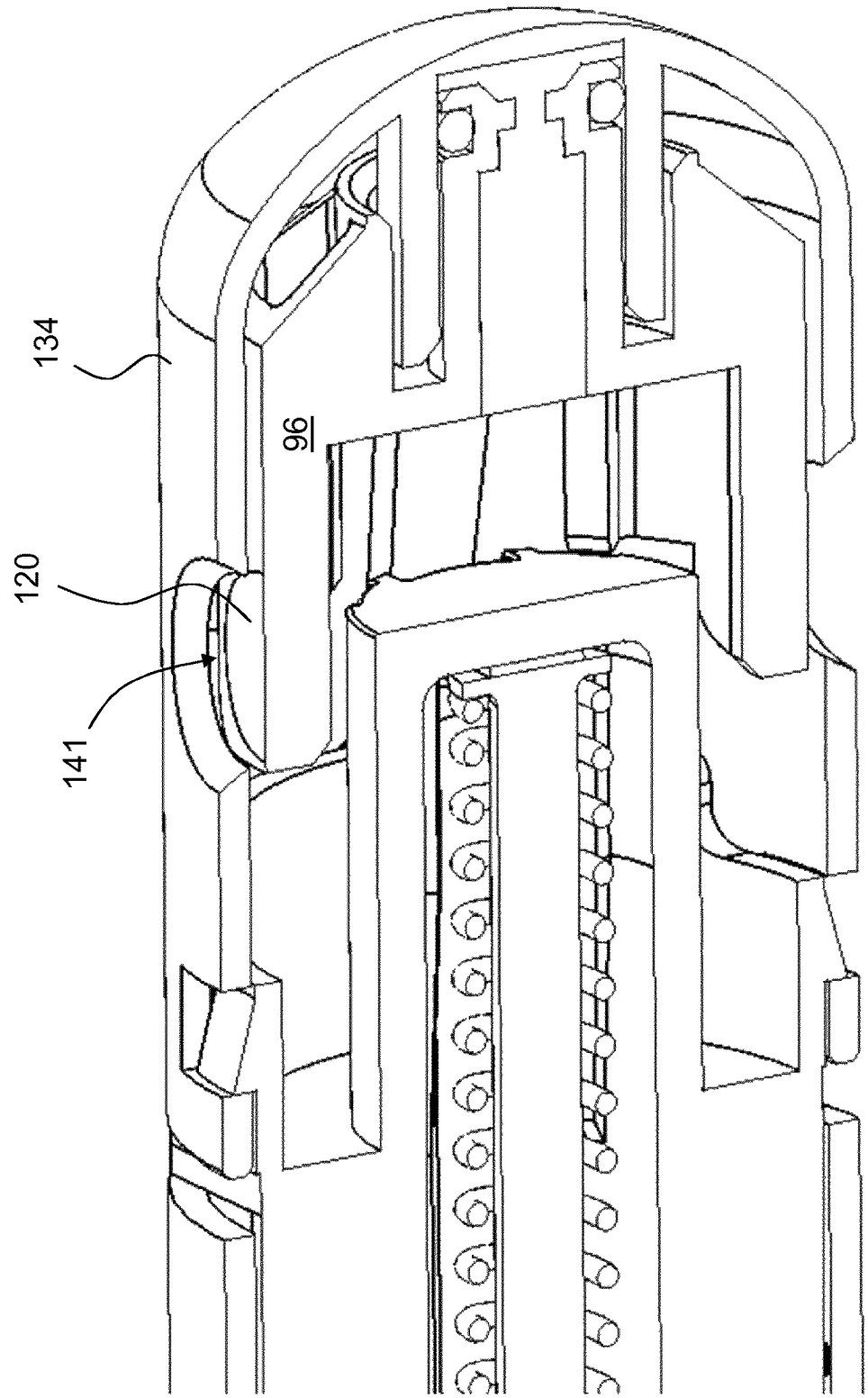

Thus the signal generating member 84 is free to move and accelerate due to the force of the force element, along the distance d. The distal movement of the signal generating member causes an interaction between the signal generating member and the end wall 108 such that the at least one feedback signal is generated. The interaction is an audible and/or tactile impact. The audible and/or tactile impact is generated when the signal generating member 84 hits the end wall 108 of the post 106 as seen in FIG. 15. The impact creates an audible as well as a tactile signal, which signal will indicate to the user that the injection sequence has come to an end and that it is safe to remove the device from the dose delivery site. Further, since the delay unit 96 has been moved in the distal direction in relation to the housing as described, the visual indicia 120 of the elements 116 of the delay unit 96 have been moved distally such that they are aligned with the windows 141 visible through the distal housing 134, FIG. 16, which further indicates to the user that injection sequence has ended and that it is safe to remove the device. The visual indicia may later be used to indicate that the device is spent and needs to be discarded. In that respect, the visual indicia may be a bright colour that is clearly visible.

As the user removes the device from the delivery site, the medicament delivery member guard 36 moves in the proximal direction, relative to the housing 10, biased by the medicament delivery member guard spring 42. This in turn causes the protrusions 48 of the arms 40 to move along the guide ridges 52 of the rotator 50, whereby the protrusions 48 will pass the wedge-shaped protrusions 54 due to the flexing action of the tongues 56. The passing of the protrusions 54 will cause the medicament delivery member guard 36 to be locked in its extended position, thereby preventing any unintentional contact and possible injury with the medicament delivery member. The device may now be discarded in a safe manner.

In an alternative embodiment (not shown) the delay female member is integral with (or attached to) the delay unit 96 and the delay male member is arranged to the inner proximally directed surface 136 of the distal housing 134.

It is to be understood that the embodiment described above and shown in the drawings is to be regarded only as a non-limiting example of the invention and that it may be modified in many ways within the scope of the patent claims.

The invention claimed is:

1. A medicament delivery device, comprising:
   a signal generating assembly comprising a signal generating member and a force element;
   a plunger rod, wherein the force element is arranged tensioned between said signal generating member and the plunger rod for moving the plunger rod and the signal generating member; and
   a signal delaying assembly positioned distal to the plunger rod and the force element, the signal delaying assembly comprising:
   a delay female member containing a fluid,
   a delay male member having at least one passage,
   a delay unit connected to the delay female member or to the delay male member, and
   a support element releasably connected to the delay unit,
   wherein a relative movement between the male member and the female member and towards each other causes a transfer of said fluid from said female member through the at least one passage for slowing said relative movement,
   wherein the delay unit is movably arranged in relation to the support element from a delaying position in which the delay unit is in contact with the support element and with the signal generating assembly, to a released position in which the delay unit is disconnected from both the support element and the signal generating assembly, and
   wherein the relative movement between the delay unit and the support element to the released position causes the signal generating assembly to generate at least one feedback signal indicating that a dose of medicament from the medicament delivery device has been completely delivered.

2. The medicament delivery device of claim 1, wherein the relative movement between the delay female member and the delay male member causes the relative movement between the delay unit and the support element from the delaying position to the released position.

3. The medicament delivery device of claim 1, wherein the delay unit comprises a flexible arm and wherein a free end of the flexible arm is arranged with an inwardly directed ledge.

4. The medicament delivery device of claim 3, wherein the delay unit is longitudinally movable in relation to the support element from the delaying position in which the flexible arm is in contact with the support element and in which the inwardly directed ledge is in contact with the signal generating assembly, to the released position in which the flexible arm is disconnected from the support element and in which the inwardly directed ledge is disconnected from the signal generating assembly by a radial movement of the flexible arm in relation to the support element.

5. The medicament delivery device of claim 1, wherein the signal generating member is releasably connected to a holding unit of the medicament delivery device, and wherein a pre-determined proximal and longitudinal movement of the plunger rod in relation to the holding unit allows the signal generating member to be released such that the force element forces a distal movement of the signal generating member in relation to the holding unit.

6. The medicament delivery device of claim 5, wherein the delay unit is in contact with the signal generating member such that the distal movement of the signal generating member causes the delay unit to move from the delaying position to the released position.

7. The medicament delivery device of claim 6, wherein the delay unit in the released position disconnects from both the support element and the signal generating member whereby the signal generating member is forced distally in relation to the support element and the delay unit by the force element.

8. The medicament delivery device of claim 7, wherein the delay unit comprises a visual indicia, such that when the delay unit is in the released position, said visual indicia is visible to a user.

9. The medicament delivery device of claim 5, wherein the distal movement of the signal generating member causes an interaction between the signal generating member and a relatively fixed surface such that the at least one feedback signal is generated.

10. The medicament delivery device of claim 9, wherein said interaction is an audible impact.

11. The medicament delivery device of claim 9, wherein said interaction is a tactile impact.

12. The medicament delivery device of claim 1, wherein the fluid comprises a highly viscous fluid.

13. The medicament delivery device of claim 1, wherein the medicament delivery device comprises an autoinjector.

* * * * *